United States Patent [19]

Schulze et al.

[11] Patent Number: 5,514,156

[45] Date of Patent: May 7, 1996

[54] COLLAPSIBLE ENDOSCOPIC FORCEPS

[75] Inventors: Dale Schulze, Lebanon, Ohio; Kirsten Huss, Ahrensburg; Axel Winkel, Quickborn, both of Germany

[73] Assignee: Ethicon Endo-Surgery, Inc., Cincinnati, Ohio

[21] Appl. No.: 226,806

[22] Filed: Apr. 12, 1994

[30] Foreign Application Priority Data

May 25, 1993 [DE] Germany .................... 43 18 951.2

[51] Int. Cl.⁶ .................................................. A61B 17/00
[52] U.S. Cl. ........................................... 606/205; 604/105
[58] Field of Search ..................... 606/205–207, 606/170, 198; 604/105; 128/17

[56] References Cited

U.S. PATENT DOCUMENTS

| 86,016 | 1/1869 | Howell | 606/206 X |
|---|---|---|---|
| 3,667,474 | 6/1972 | Lapkin et al. | 606/170 X |
| 3,857,395 | 12/1974 | Johnson et al. | 606/198 |
| 4,763,669 | 8/1988 | Jaeger | 606/198 |
| 5,171,258 | 12/1992 | Bales et al. | 606/205 |
| 5,209,747 | 5/1993 | Knoepfler | 606/205 X |
| 5,209,755 | 5/1993 | Abrahan et al. | 606/207 X |
| 5,350,391 | 9/1994 | Iacovelli | 606/207 X |
| 5,353,784 | 10/1994 | Nady-Mohamed | 606/198 X |
| 5,368,606 | 11/1994 | Marlow et al. | 606/207 X |
| 5,403,343 | 4/1995 | Sugarbaker | 606/207 |

FOREIGN PATENT DOCUMENTS

| 0507622 | 10/1992 | European Pat. Off. | A61B 17/28 |
|---|---|---|---|
| 0513471 | 11/1992 | European Pat. Off. | A61B 17/32 |
| 0541930 | 5/1993 | European Pat. Off. | A61B 17/28 |

*Primary Examiner*—Stephen C. Pellegrino
*Assistant Examiner*—Nancy Mulcare
*Attorney, Agent, or Firm*—Paul A. Coletti

[57] ABSTRACT

An endoscopic gripper consists of a guide tube with an operating device arranged at the proximal end and a pair of gripper jaws located at the distal end, which pair of gripper jaws are connected to each other by joint means in such a way that an opening and closing of the gripper jaws via tension or pressure means is made possible. Each of the gripper jaws is formed from segments and the segments are linked together by joints in such a way that a swivelling of the individual segments among each other between an unfolded position guaranteeing the operability of the gripper and a folded-together position is made possible. The segments are unfoldable by another tension means or by a pressure means after the positioning of the gripper at the surgical object.

4 Claims, 5 Drawing Sheets

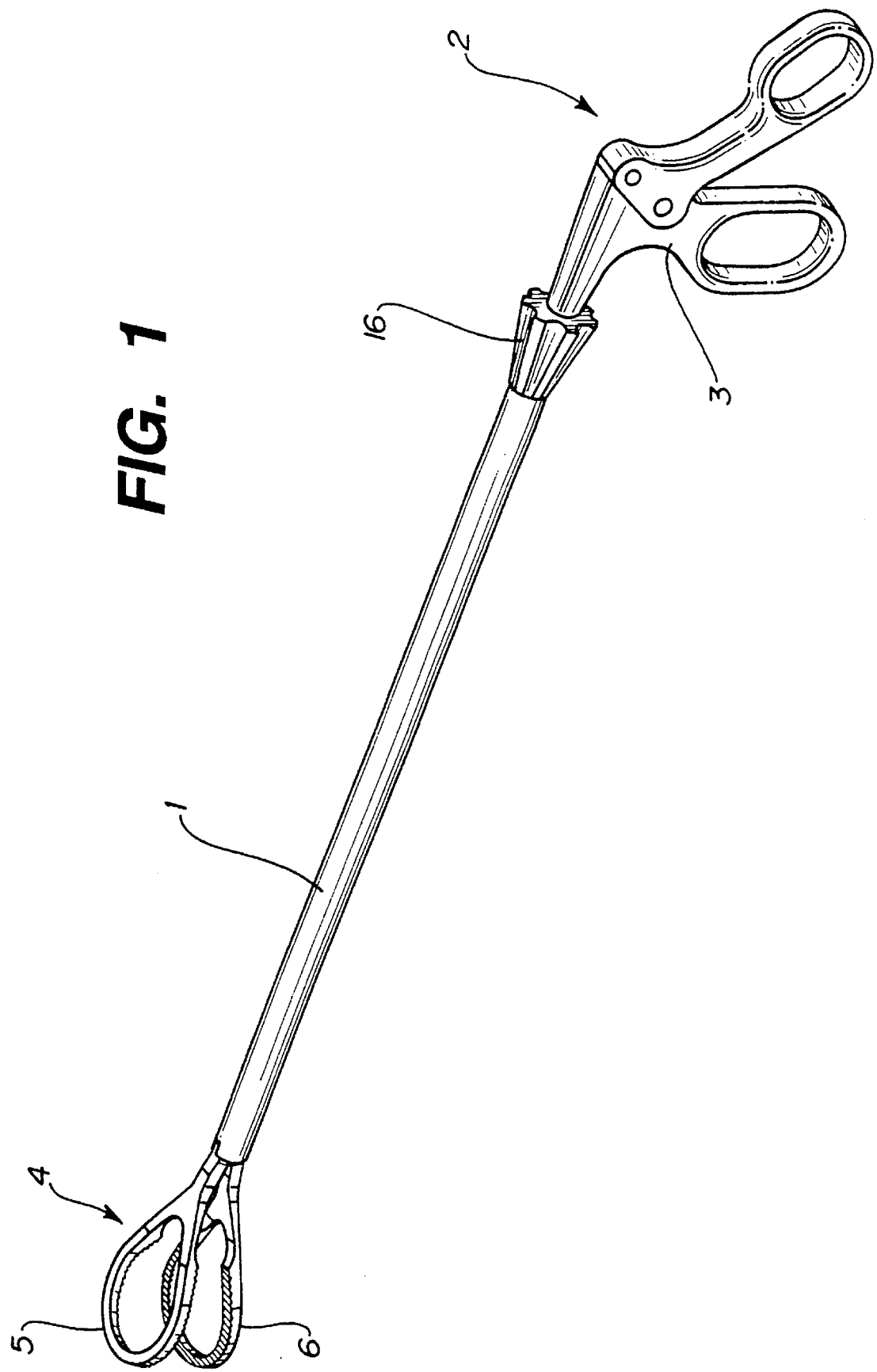

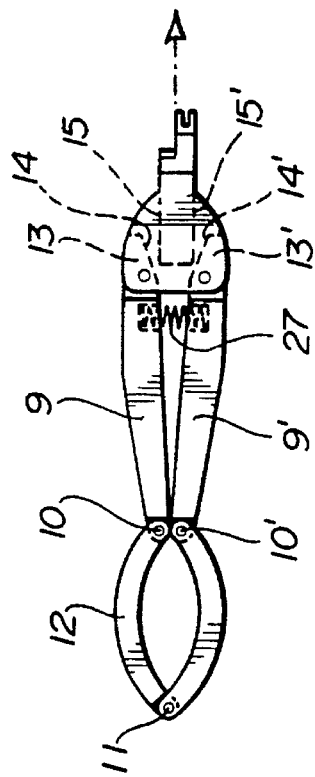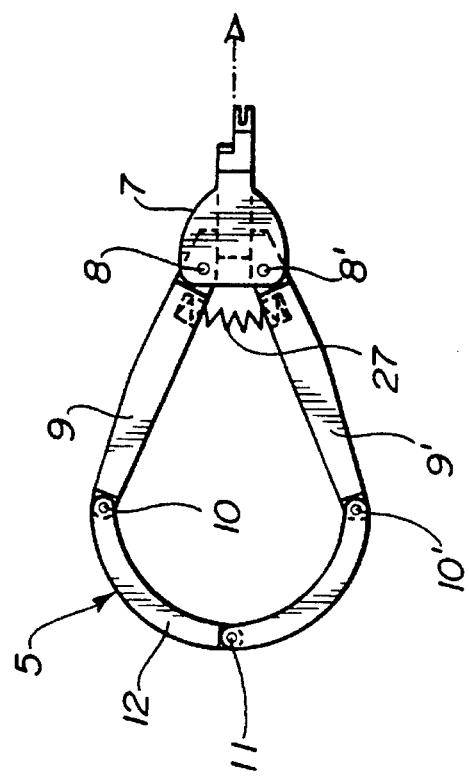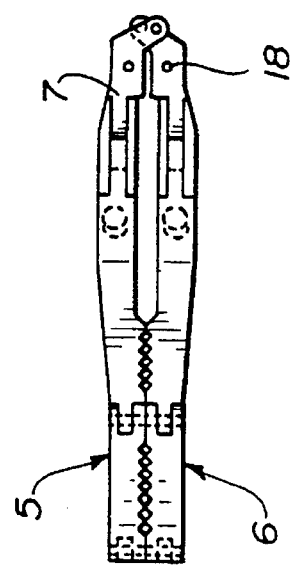

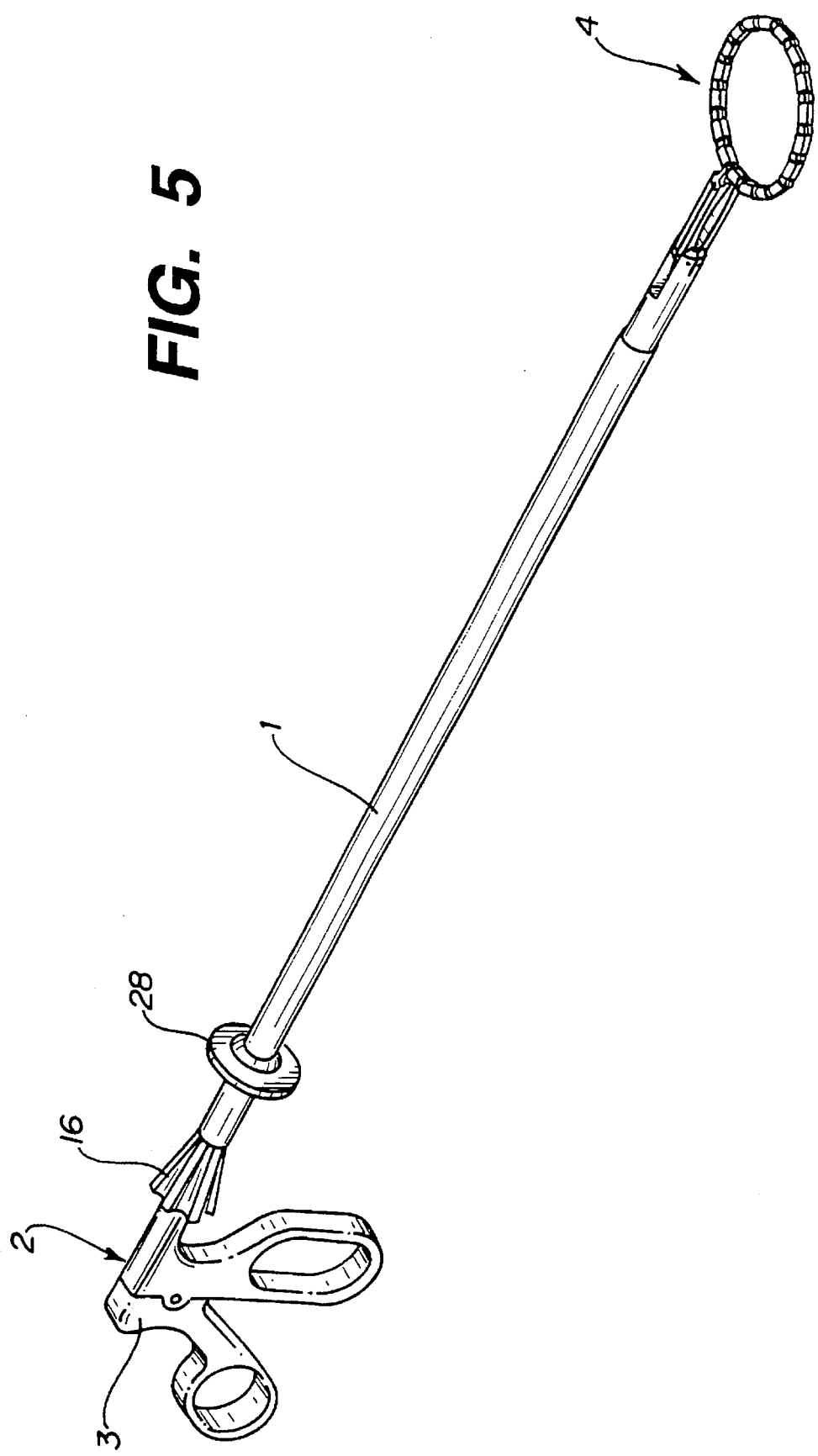

5,514,156

COLLAPSIBLE ENDOSCOPIC FORCEPS

RELATED APPLICATION

This invention claims priority from DE P 43 18 951.2, filed May 25, 1993, incorporated herein by reference.

BACKGROUND OF THE INVENTION

The invention relates to a surgical instrument for gripping and holding objects in the inside of the body, in particular for laparoscopic operations.

Numerous surgical instruments are known which are used to manipulate tissue. The tool designed in the form of forceps is connected to a rigid or flexible tube and is actuated, by an operating device arranged at the other end of the tube.

In laparoscopic surgery, a disadvantage of such instruments is that limits are placed on the size of the distal tool by the fact that the surgical apparatus must be introduced into the inside of the body through a cannula. These cannulae normally have a diameter of 10 to 20 mm. As a result, the gripper jaws of the forceps can only be of a very small design and consequently are suitable solely for such applications as the removal of tissue samples from the human body. However, the gripping and holding of other surgical objects in the body requires larger area gripping and holding elements.

The object of the invention, therefore is, to create an endoscopic gripping device whose gripper jaws can be introduced in the folded-together position through a cannula into the inside of the body and then, before the positioning at the surgical object, be enlarged into a position of operational certainty.

SUMMARY OF THE INVENTION

The endoscopic forceps or gripper described herein consists of a guide tube with an operating device arranged at the proximal end and a pair of gripper jaws located at the distal end. The pair of jaws are connected to each other by joint means in such a way that an opening and closing of the gripper jaws is made possible via tension or pressure means which are actuable via the operating device. Each of the gripper jaws is formed from segments, each of the gripper jaws preferably consisting of a ring formed from these segments. The segments are linked together by joints in such a way that a swivelling of the individual segments is possible between an unfolded or open position and a folded-together or closed position. The segments can be unfolded by tension after the positioning of the gripper at the surgical object site.

In one version of the invention, the ring consists of a pair of limbs housed symmetrical in a headpiece swivellable about joints and the segments arranged convexly between the free ends of the limbs, connected by other joints, in the form of a half-ring, divided along a symmetrical axis. The limbs display an inwardly directed support surface, which corresponds with an element located in the headpiece and limits the unfolding of the limbs. Arranged between the limbs is a compression spring which spreads the limbs apart. The headpieces allocated to the ring in question are linked together by yet another joint, and are connected to the operating device via actuation means which effect an opening and closing of the forceps gripper jaws.

In another version of the invention, the ring consists of a number of rod-shaped segments. The ends of the segments display slots running in the plane of a ring. Roll-shaped joint pieces with an axis running perpendicular to the ring plane are inserted into the slots between the neighboring ends of the segments. Both the segments and the joint pieces are provided with bores which, aligned with each other, allow passage therethrough of a bracing wire secured to the bracing element of the distal end of the instrument.

DESCRIPTION OF THE DRAWINGS

The invention is to be described in more detail with reference to an embodiment. The associated drawings show:

FIG. 1 a perspective view of the endoscopic forceps according to the invention in the operating position;

FIG. 2 a plan view of one of the gripping elements in the operating position;

FIG. 3 a side view of FIG. 2;

FIG. 4 a plan view of one of the gripping elements in a folded-together form allowing guidance through a cannula;

FIG. 5 a perspective representation of a second version of the endoscopic gripper in the operating position;

DETAILED DESCRIPTION OF THE INVENTION

Figure 6:
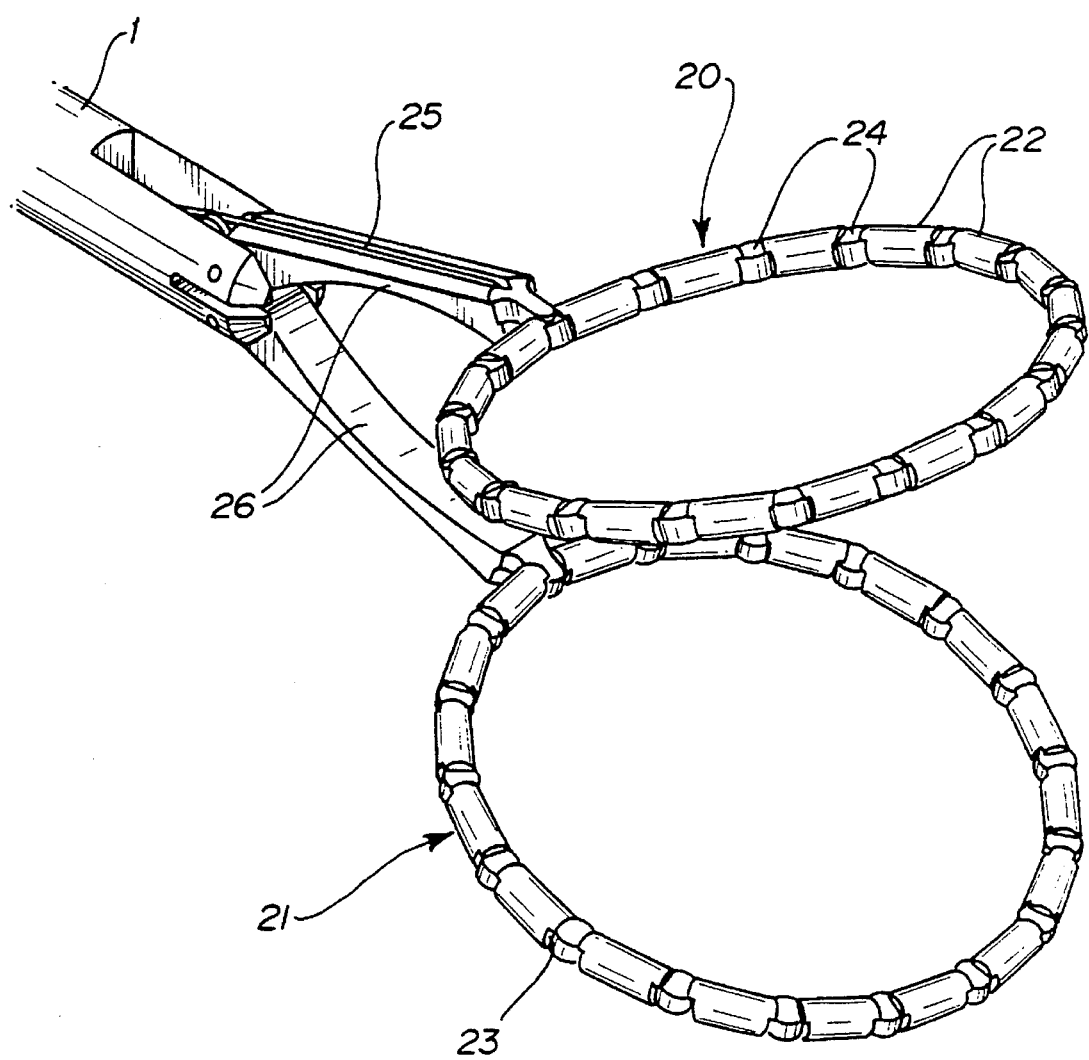
FIG. 6 a representation of the gripping elements according to FIG. 5.

The endoscopic gripper or forceps of the present invention consists in its most essential elements of a guide tube 1 with a diameter which enables an introduction endoscopically within the body through a customary cannula. Arranged at the proximal end of the guide tube 1 is the operating device 2 which is formed from a two-part shears-like handle 3, while the jaws 4 are allocated to the distal end.

The gripper or forceps jaws 4 according to a first embodiment according to FIGS. 1–4 are formed from an upper and a lower ring 5, 6 which lie congruently one above the other. The surfaces of the rings 5, 6 which face one another display a toothing which increases the grip of the jaws 4 and thus improves the gripping and holding properties of the gripper according to the invention.

It can be seen that in the operating position, the gripping elements of the jaws are of a diametrical size which is larger than the dimension of a typical cannula. It is therefore necessary to fold the gripping elements together to a suitable size in order to push them through the cannula into the inside of the body.

FIG. 2 shows the upper ring 5 in the operating position. It is formed from several segments which are connected jointwise to each other in such a way that the joints allow a swivelling of the segments among each other in a plane. The ring 5 starts from a headpiece 7 which displays two joints 8, 8' lying symmetrical to the longitudinal axis of the gripper. At these joints 8, 8', levers 9, 9' are swivellably connected thereto.

The free ends of the levers 9, 9' are bridged by a half-ring-shaped segment 12 which is divided in its center. The connecting points between the ends of the levers 9, 9' and the corresponding junction points of the half-ring-shaped segment 12 are formed by joints 10, 10'. The connection point of the divided segment 12 is also designed as a joint 11. The axes of the joints 10, 10' and 11 run parallel to the axis of the joints 8, 8' and thus guarantee a swivelling of the individual segments in the plane of the ring 5, 6. A spring 27 spreads the levers 9, 9' apart. It should be noted that lower ring 6 is designed correspondingly.

The endoscopic gripper is made to operate in the manner described below:

The ring 5 is folded together by hand prior to the introduction of the gripper into the cannula, the limbs 9, 9' being swivelled towards each other. The consequence of this swivelling is that the half-ring-shaped segment 12 folds in the joint 11 and the joints 10, 10' come into contact proximity. The folded-together ring 5 assumes a slim shape as seen in FIG. 4.

At the same time, the ring 6 is folded together in the same way. In this position, the pair of gripper jaws has its greatest elongation which allows them to be guided through the cannula into the inside of the body.

The pair of jaws is introduced manually by the operator into the area of the inside of the body that is of interest and is made operational there. After the emergence from the cannula, the half-ring-shaped segment 12 is unfolded by the force of spring 27 in the inside of the body and the limbs 9, 9' swivel outwards in the joints 8, 8' to the point where legs 13, 13' are resting with their supporting surfaces 14, 14' against the element 15, 15' of the headpiece 7. The clamping jaw has now reached its necessary operability; it is maintained thereat by the spring 27.

In the same way, ring 6 is also unfolded. Both gripper jaws are operated by opening or closing around the joint 18 by suitable tension or pressure means which are connected to the operating device 2.

Figure 7:
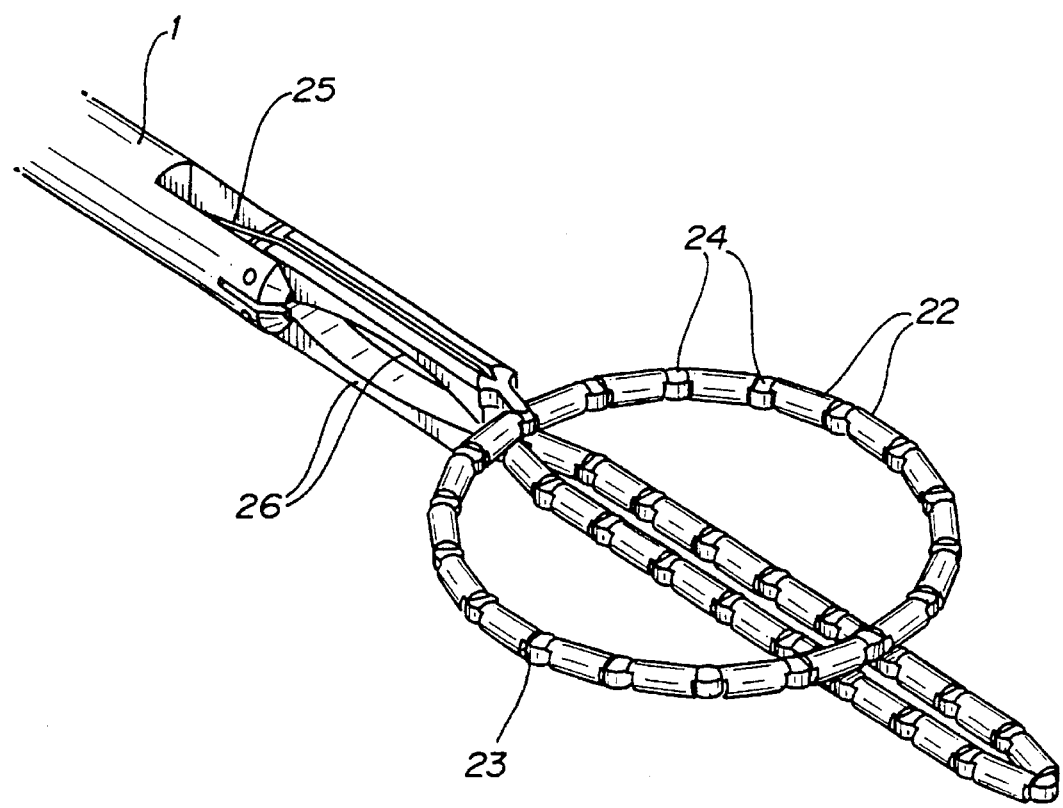
FIG. 7 a view of FIG. 6 in which the upper clamping jaw is unfolded and the lower clamping jaw is folded together.

Another version of an endoscopic forceps or gripper is described in FIGS. 5 to 7. Here, too, the gripper jaws consist of rings 20, 21, each of the rings 20, 21 being formed from a number of rod-shaped segments 22. The ends of the segments 22 display slots 23 running in the plane of the ring. Roll-shaped joint pieces 24, with an axis running perpendicular to this plane are inserted into the neighboring slots 23. Both the segments 22 and the joint pieces 24 are provided with bores which, aligning with each other, allow the guiding through of a tensioning or bracing wire 25, whose ends are secured to a bracing element 28. The bracing element 28 is displaceable in the axial direction of the guide tube 1 and may be locked in its distal or proximal positions.

As shown at the lower ring 6 according to FIG. 7, the released rings 20, 21 can be folded together and thereby achieve an elongation which makes possible the introduction through a surgical cannula. After the positioning of the gripper at the surgical object, the gripper jaws are unfolded, every bracing wire 25 being tightened by proximal movement of the bracing element 28, which, of course remains outside the body.

Arranged at the distal end of the guide tube 1 is a forceps-shaped component 26, at whose free ends the gripper jaws are hinged. The gripper jaws are opened or closed through suitable well known connecting or transmission elements to the operating device 2 upon actuation of the operating device 2.

After the surgical work has ended, the bracing wire is slackened by distal movement of element 28, and the rings folds together upon withdrawal through the cannula.

With both the version according to FIG. 1 and that according to FIG. 5, a collar 16 is arranged in the vicinity of the operating device 2 on the guide tube 1 and serves to rotate the gripper jaws about the axis of the tube 1.

What is claimed is:

1. An endoscopic instrument comprising:

a guide tube, having proximal and distal ends and a diameter;

an operating device arranged at the proximal end of the guide tube;

a pair of gripper jaws arranged at the distal end of the guide tube and connected to the operating device, the gripper jaws hingedly connected to a headpiece located at the guide tube distal end;

the gripper jaws operated by force transmitting means extending through the guide tube upon actuation of the operating device; and wherein each of the gripper jaws is formed from a plurality of segments such that adjacent segments are hingedly attached to each other, said plurality of segments having a dimension in a first closed position smaller than the diameter of the guide tube and a dimension in a second open position larger than the diameter of the guide tube, each of the jaws forming a ring created by said segments and describing a plane such that the individual segments can rotate about each other in the plane of the ring; and each said ring consisting of a pair of limbs having two ends, a first of said ends attached to said headpiece by first pivot joints and said limbs attached at a second of said ends to second pivot joints, each of said second pivot joints connected to a segment, thereby completing said ring.

2. The instrument of claim 1 further comprising said limbs connected to a spring which spreads the limbs apart, said spring arranged between said limbs.

3. An endoscopic instrument comprising:

a guide tube, having proximal and distal ends and a diameter;

an operating device arranged at the proximal end of the guide tube;

a pair of gripper jaws arranged at the distal end of the guide tube and connected to the operating device, the gripper jaws hingedly connected to a headpiece located at the guide tube distal end;

the gripper jaws operated by force transmitting means extending through the guide tube upon actuation of the operating device; and wherein each of the gripper jaws is formed from a plurality of segments such that adjacent segments are hingedly attached to each other said plurality of segments having a dimension in a first closed position smaller than the diameter of the guide tube and a dimension in a second open position larger than the diameter of the guide tube, each of the jaws forming a ring created by said segments and describing a plane such that the individual segments can rotate about each other in the plane of the ring; and each said ring consisting of a number of rod shaped segments having a pair of ends each of the ends of said rod shaped segments containing slots, and each of said slots lying in the plane of said ring; and wherein each of said segments are connected by joint pieces placed in the slots of said segments, each of said joint pieces containing a bore therethrough.

4. Instrument of claim 3 wherein a tension or bracing wire is threaded through said rod-shaped segments, said bracing wire actuable at the proximal end of said instrument to exert tension on said ring.

* * * * *